US007161163B2

(12) United States Patent
Gaebel et al.

(10) Patent No.: US 7,161,163 B2
(45) Date of Patent: Jan. 9, 2007

(54) METHOD AND ARRANGEMENT FOR THE PLASMA-BASED GENERATION OF SOFT X-RADIATION

(75) Inventors: Kai Gaebel, Jena (DE); Guido Hergenhan, Jena (DE); Christian Ziener, Jena (DE)

(73) Assignee: Xtreme Technologies GmbH, Jena (DE)

( * ) Notice: Subject to any disclaimer, the term of this patent is extended or adjusted under 35 U.S.C. 154(b) by 0 days.

(21) Appl. No.: 11/045,605

(22) Filed: Jan. 27, 2005

(65) Prior Publication Data

US 2005/0169429 A1 Aug. 4, 2005

(30) Foreign Application Priority Data

Jan. 30, 2004 (DE) ...................... 10 2004 005 241

(51) Int. Cl.
*A61N 5/06* (2006.01)

(52) U.S. Cl. ............................. 250/504 R; 250/505.1; 250/498.1

(58) Field of Classification Search ..................... None
See application file for complete search history.

(56) References Cited

U.S. PATENT DOCUMENTS 5,577,092 A 11/1996 Kublak et al.
6,002,744 A 12/1999 Hertz et al.
6,647,088 B1 * 11/2003 Schmidt et al. ............... 378/34
6,711,233 B1 * 3/2004 Hertz et al. ................. 378/143
6,855,943 B1 * 2/2005 Shields ................... 250/504 R
6,882,704 B1 * 4/2005 Schriever et al. ........... 378/119
2002/0090054 A1 * 7/2002 Sogard ....................... 378/119
2004/0129896 A1 * 7/2004 Schmidt et al. .......... 250/492.2

FOREIGN PATENT DOCUMENTS

EP 0 186 491 6/1992
WO WO 97/40650 10/1997
WO WO 01/30122 4/2001
WO WO 2004/084592 9/2004

OTHER PUBLICATIONS

SPIE Proceedings, vol. 4688, pp. 619-625, "Laser plasma radiation sources based on a laser-irradiated gas puff target for x-ray and EUV lithography technologies" H. Fledorowicz, et al.
Patent Abstracts of Japan, Publication No. 2000-299196 published Oct. 24, 2000 Agency of Ind Science & Technol Shimadzu Corp (Appln No. 11-105233 Apr. 13, 1999).

* cited by examiner

*Primary Examiner*—Nikita Wells
*Assistant Examiner*—Anthony Quash
(74) *Attorney, Agent, or Firm*—Reed Smith LLP

(57) ABSTRACT

The invention is directed to a method and an arrangement for plasma-based generation of soft x-radiation, particularly for the generation of extreme ultraviolet (EUV) radiation. The object of the invention, to find a novel possibility for providing a target for a plasma-based radiation source which permits a reduction in the heating and erosion of the nozzle and therefore permits an improved temperature control at the injection device, is met according to the invention in that a closure device is arranged between the target nozzle and the interaction region which interrupts an opening for temporarily passing the target flow by mechanically moving elements, wherein at least a portion of the target flow that is provided in a reproducible manner is separated in order to interact with the energy beam only during those time intervals in which an optical transmission from the interaction region to the target nozzle is prevented by the closure device.

26 Claims, 4 Drawing Sheets

METHOD AND ARRANGEMENT FOR THE PLASMA-BASED GENERATION OF SOFT X-RADIATION

CROSS-REFERENCE TO RELATED APPLICATION

This application claims priority of German Application No. 10 2004 005241.7, filed Jan. 30, 2004, the complete disclosure of which is hereby incorporated by reference.

BACKGROUND OF THE INVENTION a) Field of the Invention

The invention is directed to a method and an arrangement for plasma-based generation of soft x-radiation, particularly for the generation of extreme ultraviolet (EUV) radiation, in which a target flow of defined portions which is made available in a reproducible manner is interacted with a pulsed energy beam for exciting radiation-emitting plasma, wherein the interaction results in the generation of a radiation-emitting plasma. The invention is preferably applied in radiation sources with high repetition rates, preferably in radiation sources for semiconductor lithography.

b) Description of the Related Art

Plasma-based radiation sources in which the plasma is generated by introducing energy into a target preferably comprise a target flow that is injected into a vacuum chamber. The plasma is then generated at a short distance from the place of injection (nozzle) by interaction with a pulsed energy beam. Control of the process parameter of temperature is critically important particularly when using a target flow of liquid xenon at temperatures around −100° C. in order to ensure the stability of the target flow. However, the stability of the target is drastically reduced by the heating and erosion of the target nozzle over increasing operating periods or when the pulse rate of the plasma excitation is increased, so that the nozzle only has a short life.

In the prior art relating to the generation of radiation by plasma generation by means of an energy beam (usually a laser beam), plasma generation from mass-limited targets has found acceptance because such targets minimize unwanted particle emission (debris) compared with other types of targets. A mass-limited target is wherein the particle number in the region of interaction between the target and energy beam is limited to the order of magnitude of the ions used for generating radiation. A droplet generator is often used to generate mass-limited targets.

In this connection, EP 0 186 491 B1 describes the excitation of individual droplets, i.e., exactly one droplet is impinged upon per energy pulse. The droplets have the same order of magnitude as the laser focus. Because of constantly occurring variations in the droplet frequency, it is necessary to detect the droplet target and to synchronize with the laser pulses.

Further, targets in the form of clusters (U.S. Pat. No. 5,577,092), gas puffs (H. Fiedorowicz, SPIE Proceedings, Vol. 4688, 619) or aerosols (WO 01/30122) have been described for plasma generation. However, the average density of such targets in the focus volume is substantially less than in liquid targets or solid targets because the target comprises microscopic particles or is in gaseous form. Further, the target divergence is generally so big (opening angle of several degrees) that the average target density decreases rapidly with increasing distance from the nozzle and an efficient coupling in of the energy beam is possible exclusively in the immediate vicinity of the nozzle. The disadvantageous stressing of the nozzle mentioned above is accordingly inevitable.

While devices with a continuous target jet (liquid or frozen jet) such as those described in WO97/40650, for example, allow a relatively large working distance from the nozzle, they are susceptible to shock waves. This means that the coupled-in radiation-generating energy pulse causes hydrodynamic disturbance extending relatively far along the jet axis and the characteristics of the continuing jet for optimal plasma generation and radiation generation are impaired. This disturbance prevents a high pulse repetition frequency because it is necessary to wait for the disturbance to die away for the next pulse.

OBJECT AND SUMMARY OF THE INVENTION

It is the primary object of the invention to find a novel possibility for providing a target for a plasma-based radiation source which adequately protects the target nozzle against electromagnetic radiation and high-energy particles from the generated plasma, i.e., which permits a reduction in the heating and erosion of the nozzle and therefore permits an improved temperature control at the injection device.

In a method for plasma-based generation of soft x-radiation, particularly for the generation of extreme ultraviolet (EUV) radiation, in which a target flow comprising defined portions which is provided in a reproducible manner is made to interact with a pulsed energy beam in order to excite radiation-emitting plasma, wherein the interaction results in the generation of a radiation-emitting plasma, the above-stated object is met, according to the invention, in that the target flow is temporarily interrupted by a closure device, wherein the interruption is carried out at least during the interaction of the energy beam with a portion of the target flow located in the interaction region, in that in the interaction region the energy beam impinges on a portion of the target flow which is separated in a defined manner and whose material is converted (at least for the most part) into radiation-generating plasma, and in that the closure device is opened during the pauses between the pulses of the energy beam in order to allow other portions of the target flow to pass into the interaction region of the energy beam.

Liquid target material is advantageously injected into the vacuum chamber as a continuous target flow through a target nozzle, this target being divided into defined target portions by means of the closure device. For this purpose, a periodic movement of the closure device is advisably carried out in such a way that the target flow is alternately interrupted and released and the interruption is carried out so as to be synchronized with the pulses of the energy beam. By expanding the closure device, the vacuum chamber is advantageously divided in a gastight manner into an injection chamber and an interaction chamber at least partially or completely and temporarily, wherein a pressure difference is generated from the injection location to the interaction region or a pressure is adjusted in the interaction chamber that is lower than the pressure in the injection chamber.

Further, in an arrangement for plasma-based generation of soft x-radiation, particularly for the generation of extreme ultraviolet (EUV) radiation, containing a target generator with a target nozzle for providing a target flow with small divergence which is provided in a reproducible manner in a vacuum chamber and a pulsed energy beam which is focused on defined portions of the target flow at an interaction point in order to generate a radiation-emitting plasma, the above-stated object is met, according to the invention, in that a closure device is arranged between the target nozzle and an interaction region located around the interaction point, which closure device has at least one opening for passing the target flow and which temporarily interrupts the passage of the target flow through the opening by means of mechanically movable elements, wherein at least a portion of the target flow that is provided in a reproducible manner from the target nozzle is separated for interaction with the energy beam, and in that the pulsed energy beam is synchronized with the closure device in such a way that portions of the target flow that have passed into the interaction region are converted into radiation-emitting plasma only during those time intervals of the energy beam during which an optical transmission and particle transmission from the interaction region to the target nozzle is prevented by the closure device.

The closure device advantageously has a rotating diaphragm with at least one opening for passing the target flow. The rotating diaphragm has an axis of rotation outside of and parallel to the axis of the target flow so that openings and closed areas of the diaphragm are located in the target flow in an alternating manner.

In another embodiment form of the invention, the closure device has a closure plate which moves in a translatory manner for temporarily closing the opening allowing the passage of the target flow. The closure plate is movable linearly in a plane orthogonal to the axis of the target flow so that the opening is alternatively closed or released by the closure plate for passing the target flow.

The closure device can advisably also have a plurality of movable closure plates for closing the opening. The closure plates are movable in an orthogonal plane relative to the axis of the target flow in such a way that they meet in the axis of the target flow for temporarily closing the opening.

In another advantageous construction, the closure device is formed by a rotating cylinder which has its axis of rotation outside of and orthogonal to the axis of the target flow. The cylinder has at least one opening extending through its outer jacket for passing the target flow, so that the opening and closed jacket of the cylinder is alternately located in the target flow. In this connection, it is possible alternatively that the rotating closure device formed in this way is a hollow cylinder or a solid cylinder.

Additional stationary mechanical means which expand the surface area of the closure device are advantageously arranged in the vacuum chamber for enlarging the shaded area of the target nozzle. This is preferably carried out by means of a dividing wall which at least partially divides the vacuum chamber into an injection chamber and an interaction chamber by expanding the closure device. In this case, means for gradually reducing pressure to a suitable working pressure in the interaction zone are advantageously provided in the interaction chamber.

In an advantageous variant, the dividing wall is constructed as a wall for completely separating the interaction chamber from the injection chamber so that a pressure difference can be generated from the target nozzle to the interaction region. The dividing wall is preferably constructed as a wall for temporary gastight separation of the interaction chamber from the injection chamber so that a pressure can be adjusted in the interaction chamber that is lower than the pressure in the injection chamber.

In order to prevent impermissible heating of the closure device and/or of the dividing wall, the latter are advantageously outfitted with additional cooling means.

It has proven advantageous when the target flow reaches the location of the closure device as a continuous target jet with low divergence. However, it is also possible for it to enter the closure device (in a suitably synchronized manner) in the form of a discontinuous target volume.

The target flow is advisably in liquid or solidified aggregate state in the interaction region. A liquefied gas or gas mixture, preferably with at least one inert gas, e.g., xenon, is advantageously used to form the target flow through the target nozzle. However, the target can also be formed by a liquid metal or a liquid metal compound and can advantageously contain tin. Similarly, lithium, fluorine, gallium to selenium, indium to strontium, or compounds thereof, particularly saline solutions or fluoro-fomblin, can be used as target materials.

The energy beam for plasma generation is preferably a laser beam. However, an electron beam or ion beam is also suitable for exciting the hot plasma.

The basic idea of the invention consists in that the erosion of the injection device (target nozzle) is caused by particles from the plasma as was shown in experimental investigations on plasma-based radiation sources that are ignited by energy pulses (e.g., a high-power laser). This nozzle erosion reduces the quantity of the plasma ignitions which can be realized and for which a stable target can be formed (very limited life time of the target nozzle). Further, due to the high output of the short-wavelength radiation emitted by the plasma, the target nozzle is additionally heated which makes it more difficult to control the process parameter of temperature. However, controlling the process parameters as exactly as possible is crucial for the directional stability of the target flow. Therefore, the invention makes use of a protective device which is arranged as a mechanical closure so as to be movable between the target nozzle and the plasma and therefore at least temporarily interrupts particle radiation and energy radiation from the plasma to the target nozzle. By interrupting this line of sight between the plasma and target nozzle during plasma generation, the radiation emitted by the plasma is prevented from reaching the injection device and in particular is prevented from heating the target nozzle. When the interruption lasts for some time after the plasma ignition, this appreciably reduces the particle bombardment on the target nozzle from the plasma and therefore the erosion of the target nozzle.

Further, the invention acts in particular in such a way that when a continuous low-divergence target flow is used the closure device simultaneously divides the target flow into defined portions (mass-limited individual target) in an adjustable manner, so that the individual targets can be provided for interaction with the energy beam at a substantially greater distance from the target nozzle and the erosion and radiation loading of the target nozzle is accordingly further reduced.

With a plasma-based radiation source, the invention enables a sufficient protection of the target nozzle from electromagnetic radiation and high-energy particles during the generation of the emitting plasma, i.e., the invention makes it possible to reduce the heating and erosion of the nozzle and therefore to achieve an improved temperature control at the injection device. Further, a simple division of the target flow into defined portions (mass-limited targets) is possible so that, above all, apart from increasing the distance of the interaction region from the target nozzle, the debris generated by the plasma is also reduced.

The invention will be described more fully in the following with reference to embodiment examples.

DESCRIPTION OF THE PREFERRED EMBODIMENTS

Figure 1:
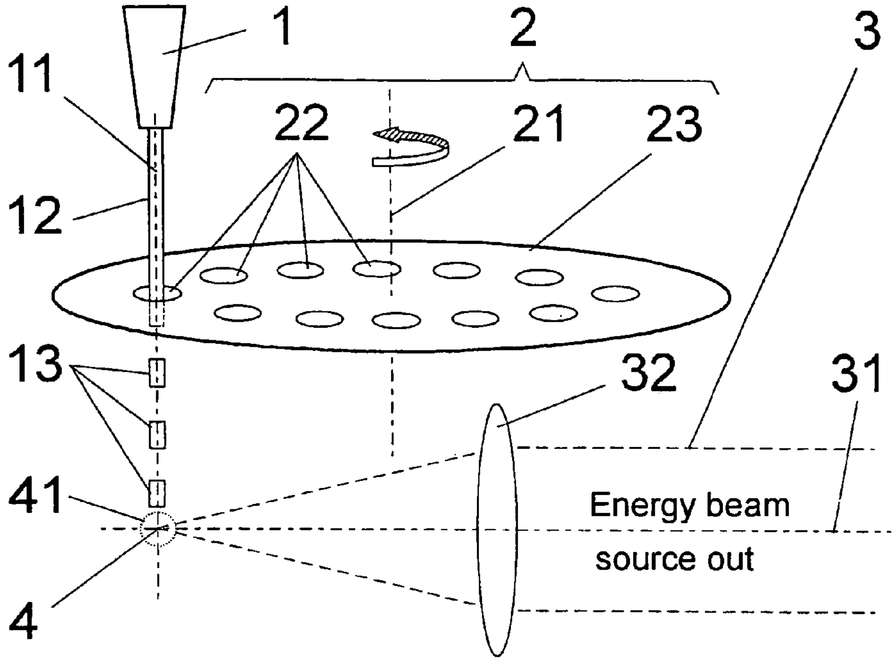
FIG. 1 is a schematic view of the arrangement according to the invention with a rotating diaphragm for protecting the target nozzle and showing a time when the target flow passes the opening of the rotating diaphragm and no laser pulse is triggered.
Figure 7:
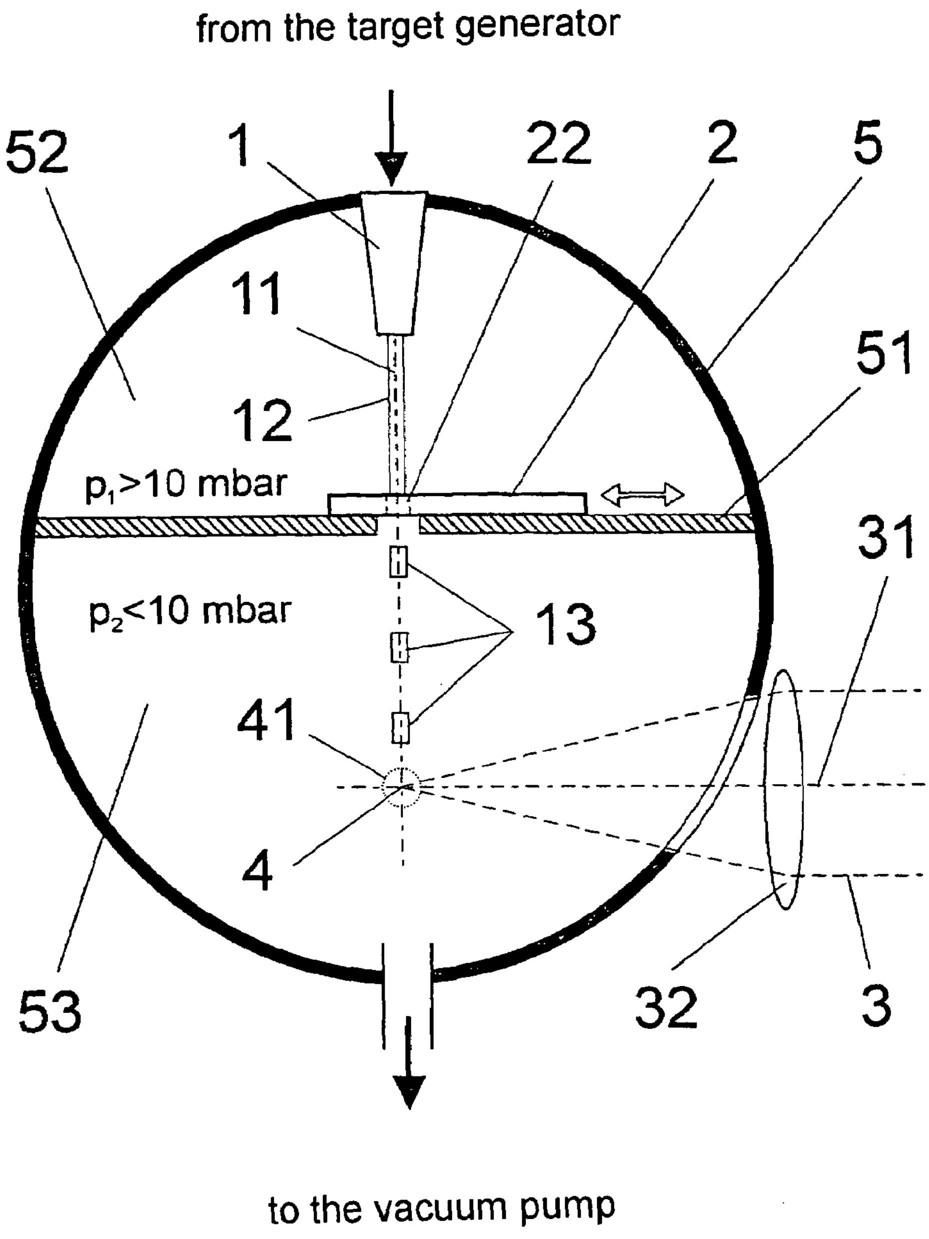
FIG. 7 shows an embodiment of the invention for a gradual reduction of pressure on the path to the interaction chamber, the interaction with the energy beam (not shown) taking place in the lower chamber.

FIG. 1 shows an arrangement for highly repetitive generation of a radiation-emitting plasma which is located inside a vacuum chamber 5 (shown only in FIG. 7). For this purpose, a low-divergence target flow 12 is generated by means of injecting a liquid target material into the vacuum chamber 5 through a target nozzle 1. When using an element (or a compound) that is in gaseous form under normal conditions for generating the target flow 12, the liquefaction of the gas (advisably inert gas, preferably xenon) is carried out at a suitable pressure and a suitable temperature before injecting into the vacuum chamber. This also applies for an element or compound that is solid under normal conditions. Since the operating point is characterized by a defined temperature and a defined pressure, the control of these parameters is crucial for a stable process. The temperature at the injection device in particular is influenced by radiative heating from the environment. A high heat output is generated by the plasma source itself when the plasma irradiates the target nozzle without hindrance, i.e., without any shading or masking of the injection device (with respect to time or space).

Depending on process conditions and on the characteristics of the target material, the injected target flow 12 can be present in the vacuum chamber 5 in continuous form (liquid or solid) or as droplets (liquid or solid) after a certain distance.

The following examples are based on, but are not limited to, a continuous target flow 12. In case of a flow of droplet targets, the closure device must additionally be synchronized with the droplet generation of the injection device so that exclusively a shielding or protective function of the closure device is effected.

In order to protect the target nozzle 1, mechanical components of a closure device 2 are periodically brought between the interaction region 41 and the injection location (target nozzle 1) in such a way that the line of sight between the two is interrupted at the moment of plasma generation and for some time thereafter. For this purpose, the target flow 12 is made to interact with a pulsed energy beam 3 in order to achieve high energy inputs and the target flow 12 between the target nozzle 1 and interaction location 4 can be interrupted at least temporarily. By protection of the target nozzle 1 is meant broadly that the radiation loading of the target nozzle 1 (by particle generation and high-energy radiation from the plasma 42) is reduced.

Energetic ions from the plasma 42 are prevented from reaching the target nozzle 1 by temporarily shading the target nozzle 1 at the moment of plasma generation and radiation generation and for some time thereafter. Erosion of the target nozzle 1 is sharply reduced in this way. At the same time, the electromagnetic radiation acting upon the target nozzle 1 is minimized by the temporary shading of the target nozzle 1.

The device for shading the target nozzle 1 simultaneously divides the target flow 12, which is initially continuous and which is susceptible to disturbance caused by plasma generation, into defined, separate portions 13. In contrast to individual droplets whose volume can only be varied slightly, the volume of a portion 13 separated from the target flow 12 in this way is adjustable in a relatively simple manner over the length of the portion 13.

The synchronization with the excitation pulse of the energy beam 3 is substantially simpler than for droplet targets in which the frequency of the droplet formation is not completely free from fluctuation.

Due to the low divergence of a target flow 12 which is provided in a reproducible manner, a relatively large working distance (on the order of several centimeters) from the target nozzle 1 can be selected.

EXAMPLE 1

Figure 2:
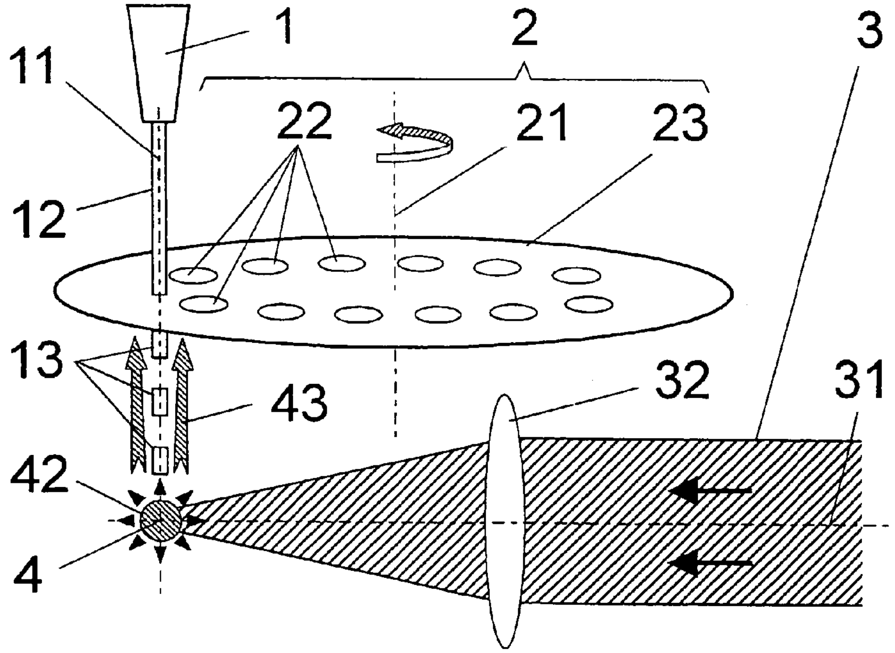
FIG. 2 is a schematic view of the arrangement according to the invention according to FIG. 1 at a later point in time during which the line of sight between the target nozzle and interaction region is interrupted by a closed area of the rotating diaphragm, the laser pulse impinges on a separate target portion, and electromagnetic radiation and energy ions cannot reach the target nozzle due to the position of the diaphragm.

FIGS. 1 and 2 show two different times during plasma-based generation of radiation in which a rotatable diaphragm 23 is arranged between the target nozzle 1 and the interaction point 4 (intersection of the target axis 11 and the energy beam axis 31) in such a way that the axis of rotation 21 of the diaphragm 23 is not located on the target axis 11 and at least one opening 22 is introduced in the diaphragm 23 which periodically releases or shades the target flow 12 temporarily during the uniform rotation of the diaphragm 23 (in this example, a plurality of openings 22 are arranged uniformly in a circle around the axis of rotation 21). In this way, the target flow 12 is divided into separate target volumes (portions 13) that reach the interaction region 41 of the target flow 12 and the energy beam 3. The interaction region 41 is defined by the intersection of the target axis 11 and the axis 31 of the energy beam 3 and the immediate surroundings thereof. The direct line of sight (free optical light path) between the interaction region 41 and the target nozzle 1 is temporarily completely interrupted by the closed areas (between the openings 22) of the diaphragm 23.

The size of the openings 22 and the ratio of the arc length within an opening 22 to the arc length of closed areas of the diaphragm 23 and the rotational speed of the diaphragm 23 can be selected in a suitable manner for adjusting the length and the distance of the target portions 13 relative to one another for the desired repetition rate and radiation yields per pulse of the energy beam 3. The radius of the arc is determined by the distance between the axis of rotation 21 of the diaphragm 23 and the target axis 11. The synchronization of the plasma generation with the interruption of the direct line of sight is carried out in such a way that the electromagnetic radiation and/or the bulk of energy ions are prevented from reaching the target nozzle 1 through closed areas of the diaphragm 23. This means that a closed diaphragm area between two openings 22 is located on the line of sight between the interaction region 41 and the target nozzle 1 during the ignition of the plasma 42 and for a certain time thereafter. The actual times depend on the plasma conditions and the geometry of the arrangement.

An embodiment of the invention with a rotatable diaphragm 23 is shown in the following by way of example. The target flow 12 has a speed $V_{jet}$ of 50 m/s (with a diameter of some 10 μm). Selecting a distance of 50 mm between the target axis 11 and the axis of rotation 21 of the diaphragm 23, a diameter of the individual opening 22 (bore hole) of 2.5 mm in each instance, an arc length between two openings 22 of 5 mm, and a rotational frequency of the diaphragm 23 of 300 Hz (18,000 RPM, comparable to a turbopump rotor) results in a portion 13 (individual target) separated from the target flow 12 with a length of 1 mm and a distance of 2 mm between two portions 13. When the interaction point 4 of the energy beam 3 lies at a distance of 5 cm below the diaphragm 23, the line of sight between the plasma 42 and the target nozzle 1 is completely blocked at the moment of plasma generation. The protection of the target nozzle 1 (according to FIG. 2) is accordingly ensured and an acceptable succession and length of the individual targets (portions 13) is adjusted at the same time.

The plasma generation is preferably carried out with a laser beam as an energy beam 3. However, an energy particle beam (electron beam or ion beam) can also be used to generate the plasma 42.

EXAMPLE 2

Linearly Moving Diaphragm Plate

Figure 3:
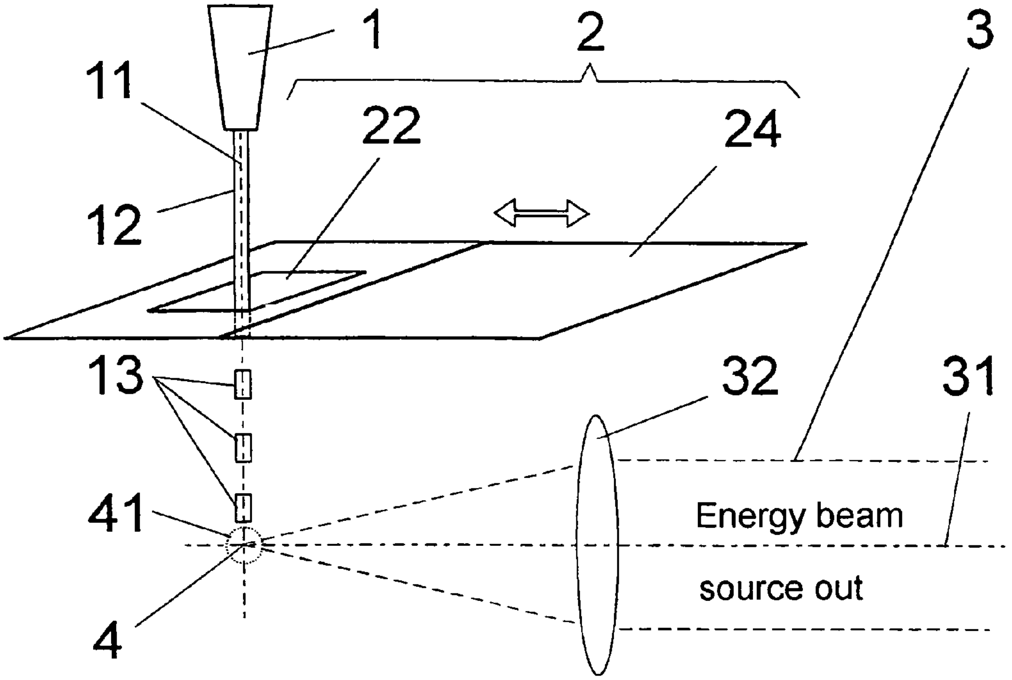
FIG. 3 is a schematic view of the arrangement according to the invention with a linearly moving diaphragm at a time when the target flow passes the diaphragm and no laser pulse strikes the target, wherein the diaphragm divides the vacuum chamber (optionally) into an injection chamber and interaction chamber by means of a gastight wall.
Figure 4:
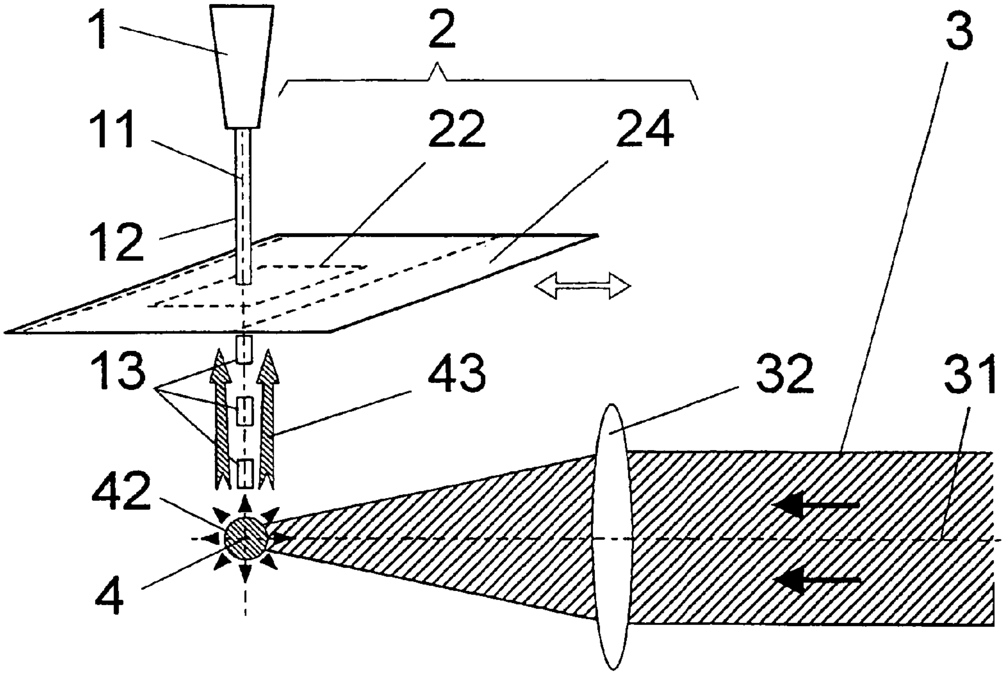
FIG. 4 is a schematic view of the arrangement according to the invention according to FIG. 3 at a time when the laser pulse strikes the target while the line of sight between the target nozzle and interaction region is blocked by the diaphragm and the energy ions and electromagnetic radiation generated in the plasma cannot reach the target nozzle.

In a second embodiment according to FIG. 3 and FIG. 4, the periodic interruption of the line of sight between the interaction area 41 and the target nozzle 1 is achieved by means of a movable diaphragm plate 24 which carries out a periodic linear movement with at least one perpendicular projection relative to the target flow 12 in such a way that an individual opening 22 is temporarily located in the axis 11 of the target flow 12 and opens the optical light path. A closed area of the diaphragm plate 24 is located on the line of sight during the ignition of the plasma 42 and for a certain time thereafter. Since the amplitude of the translation needs only to be bigger by one order of magnitude than the typical target diameters of about 20 μm, the excitation can be carried out with a piezoelectric actuating element.

It is likewise possible to interrupt the target flow 12 with two diaphragm plates 24 which are displaceable linearly relative to one another and whose closure line (not shown) lies in the axis 11 of the target flow 12.

EXAMPLE 3

Rotating Cylinder

Figure 5:
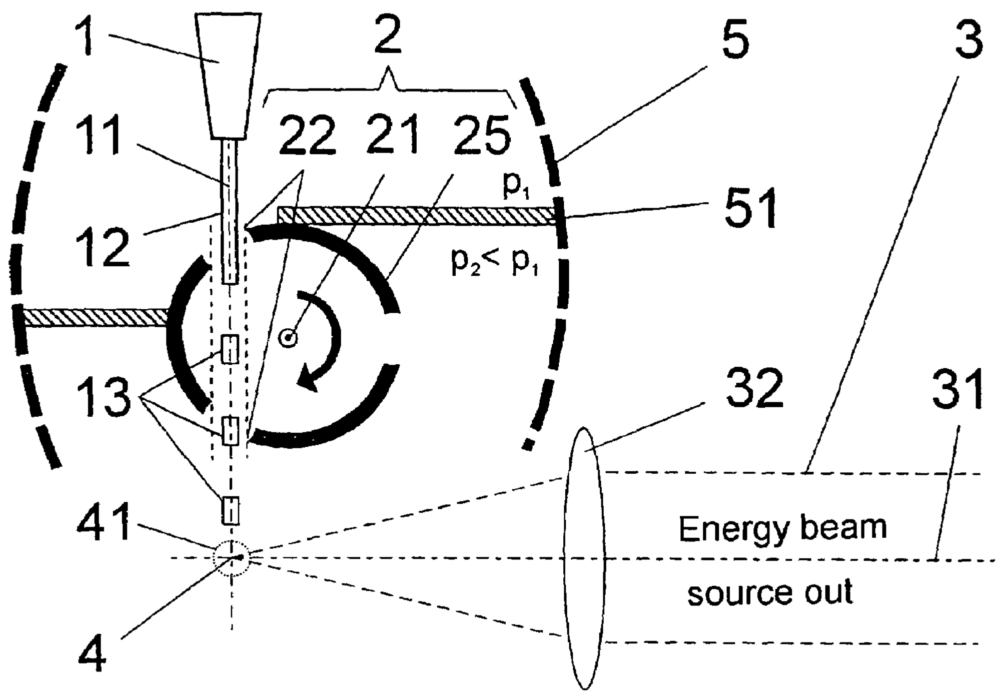
FIG. 5 is a schematic view of the invention with a diaphragm in the form of a rotating hollow cylinder at a point in time when a continuous target flow enters the hollow cylinder on the nozzle side and a target portion simultaneously exits the hollow cylinder and no laser pulse strikes the target.
Figure 6:
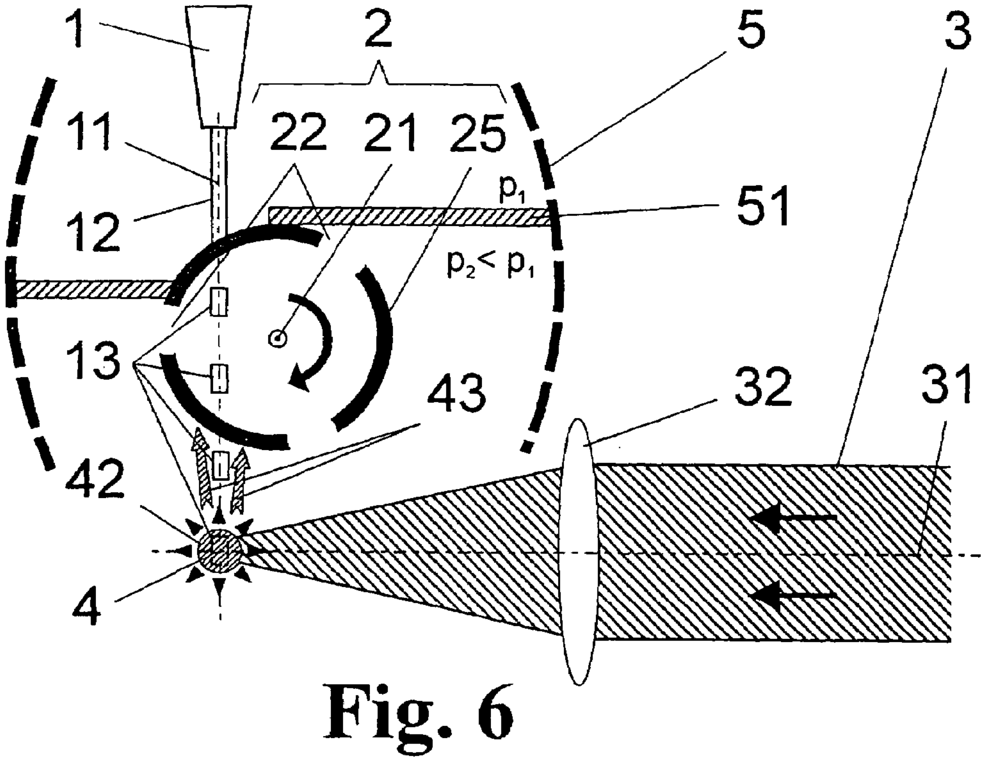
FIG. 6 is a schematic view of the invention according to FIG. 5 at a time during plasma excitation when the line of sight between the interaction region and target nozzle is blocked by closed wall areas of the hollow cylinder and the hollow cylinder is (optionally) fitted into a gastight dividing wall for dividing the vacuum chamber into an injection chamber and interaction chamber.

In another embodiment according to FIG. 5 and FIG. 6, the line of sight between the interaction region 41 and the target nozzle 1 is temporarily released or interrupted by a rotating hollow cylinder 25.

The axis of rotation 21 of the hollow cylinder 25 lies outside of the axis 11 of the target flow 12 and is oriented orthogonal to it. The hollow cylinder 25 has openings 22 in its jacket which pass parts (portions 22) of the target flow 12 along the axis 11 during at least one rotational position. For this purpose, the jacket of the hollow cylinder 25 has at least one bore hole through which a portion 13 of the target flow 12 reaches the interior of the hollow cylinder 25 and, when the linear movement of the passed portion 13 is correspondingly synchronized with the rotational movement of the hollow cylinder 25, exits the latter again and arrives in the interaction region 41. The line of sight to the target nozzle 1 is interrupted by closed jacket areas of the hollow cylinder 25 at the moment of plasma excitation by the energy beam 3 in the interaction point 4 and for some time thereafter.

The example shown in FIG. 5 where a completely open line of sight exists between the interaction region 41 and target nozzle 1 at a determined time is only a variant which also takes into account the possibility of using a solid cylinder, but which is otherwise not obligatory because an open optical light path from the target nozzle 1 to the interaction point 4 is not required for plasma generation and radiation generation. Accordingly, a solid cylinder containing one or more suitably introduced bore holes which temporarily release the target axis 11 (channel shown in dashes in FIG. 5) can be used instead of the hollow cylinder 25, although this case is not shown separately.

With a hollow cylinder 25, it is necessary only that the rotating speed is adjusted in such a way that the openings 22 in the jacket allow a target portion 13 that has arrived in the hollow cylinder 25 to exit again without obstruction along the axis 11 of the target flow 12.

Further, the closure device 2 which is represented in the example by a hollow cylinder 25 is expanded by a supplementary dividing wall 51 so that the vacuum chamber 5 (shown in dashes in FIG. 5 and FIG. 6 and indicated only partially as a support of the protective wall 51) is divided into two partial chambers, wherein a pressure drop ($p_2<p_1$) can be adjusted between the two parts of the vacuum chamber 5.

In the other constructions according to Examples 1 and 2, it is likewise possible to introduce a dividing wall 51 that supplements the closure device 2 so that the surface shading the target nozzle 1 is enlarged and a temporary gastight closure (but at least a pressure difference) is achieved between the target nozzle 1 and the interaction region 41 by dividing the vacuum chamber 5 into an injection chamber 52 and an interaction chamber 53.

A supplementary dividing wall 51 such as that shown by way of example exclusively for the third embodiment example with a rotating hollow cylinder 25 is shown again in FIG. 7 in a general view in order to illustrate the general applicability for all of the illustrated examples and the principal construction.

In this connection, FIG. 7 shows a dividing wall 51 and a closure device 2 in a vacuum chamber 5, shown schematically. In addition to the improved shading of the target nozzle 1, this arrangement permits a gradual reduction in pressure on the path of the target flow 12 to the interaction region 41.

Since a liquid target flow 12 reaches a state of nonequilibrium (vapor pressure greater than surrounding pressure) when exiting from the target nozzle 1 of the injection system in the vacuum chamber 5, a surface layer of the target flow 12 evaporates when entering the injection chamber 52. By means of a suitable aperture for the target flow 12 and the connection point of the vacuum pump (shown only schematically) in the interaction chamber 53, the lower part of the vacuum chamber 5 (interaction chamber 53) is evacuated more efficiently than the upper part (injection chamber 52). In this way, different pressures (pressure differences from the injection chamber 52 to the interaction chamber 53) are adjusted in the different parts of the vacuum chamber 5.

Further, additional means for cooling the moving diaphragms 23, 24, 25 and/or the stationary dividing wall 51 which prevent excessive heating of the closure device 2 and/or dividing wall 51 are possible in all of the embodiment examples.

While the foregoing description and drawings represent the present invention, it will be obvious to those skilled in the art that various changes may be made therein without departing from the true spirit and scope of the present invention.

REFERENCE NUMBERS

1 target nozzle
11 target axis
12 target flow
13 portion
2 closure device
21 axis of rotation
22 opening
23 rotating diaphragm
24 diaphragm plate
25 hollow cylinder
3 energy beam
31 axis (of the energy beam)
32 focusing device
4 interaction point
41 interaction region
42 plasma
42 energy radiation and particle radiation
5 vacuum chamber
51 dividing wall
52 injection chamber
53 interaction chamber

What is claimed is:

1. An arrangement for plasma-based generation of soft x-radiation, particularly for the generation of extreme ultraviolet (EUV) radiation, comprising:

a target generator with a target nozzle for generating a target flow in a reproducible and regular manner as a liquid flow of substantially linear propagation in a vacuum chamber;

a pulsed energy beam which is focused on defined portions of the target flow at an interaction point in order to generate a radiation-emitting plasma;

a closure device being arranged between the target nozzle and an interaction region located around the interaction point;

said closure device having at least one opening for passing the target flow and which temporarily interrupts the passage of the target flow through said opening by mechanically movable elements;

wherein at least a one portion of the target flow that is provided in a reproducible manner from the target nozzle is separated for interacting with the energy beam; and said pulsed energy beam being synchronized with the closure device in such a way that, during time intervals when a portions of the target flow having passed into the interaction region is converted into radiation-emitting plasma, the closure device interrupts the transmission to prevent the radiation and particles emitted from the plasma from entering and damaging the target nozzle.

2. The arrangement according to claim 1, wherein the closure device has a rotating diaphragm with at least one opening for passing the target flow, wherein the rotating diaphragm has an axis of rotation outside of and parallel to the axis of the target flow so that openings and closed areas of the diaphragm are located in the target flow in an alternating manner.

3. The arrangement according to claim 1, wherein the closure device has a diaphragm plate which moves in a translatory manner for temporarily closing the opening allowing the passage of the target flow, wherein the diaphragm plate is movable linearly in a plane orthogonal to the axis of the target flow so that the opening is alternatively covered or released by the diaphragm plate for passing the target flow.

4. The arrangement according to claim 1, wherein the closure device has a plurality of movable diaphragm plates for temporarily closing the opening that passes the target flow, wherein the diaphragm plates are movable in a plane orthogonal to the axis of the target flow in such a way that they meet in the axis of the target flow for temporarily closing the opening.

5. The arrangement according to claim 1, wherein the closure device is a rotating cylinder which has its axis of rotation orthogonal to the axis of the target flow, wherein the cylinder has at least one opening extending through its outer jacket for passing the target flow, so that the opening and closed jacket of the cylinder are alternately located in the target flow.

6. The arrangement according to claim 5, wherein the closure device has a rotating hollow cylinder.

7. The arrangement according to claim 5, wherein the closure device is a rotating solid cylinder.

8. The arrangement according to claim 1, wherein additional stationary mechanical means for shielding the nozzle from radiation and particles generated by the plasma are arranged in the vacuum chamber in such a manner that the closure device is extended laterally with respect to the axis of the target flow to effect an enlarged shaded area around the nozzle with respect to irradiation by the plasma.

9. The arrangement according to claim 8, wherein a dividing wall which expands the closure device is arranged in the vacuum chamber for dividing the vacuum chamber into an injection chamber and an interaction chamber.

10. The arrangement according to claim 9, wherein means for gradually reducing pressure to a suitable working pressure in the interaction region are provided in the interaction chamber.

11. The arrangement according to claim 10, wherein the dividing wall is constructed as a wall for completely separating the interaction chamber from the injection chamber so that there is a pressure difference from the target nozzle to the interaction region.

12. The arrangement according to claim 10, wherein the dividing wall is constructed as a wall for temporary gastight partitioning of the interaction chamber from the injection chamber so that a pressure can be adjusted in the interaction chamber that is lower than the pressure in the injection chamber.

13. The arrangement according to claim 9, wherein additional cooling means are provided for the closure device or dividing wall.

14. The arrangement according to claim 9, wherein the target flow, as a target flow that can be made available in a reproducible manner, reaches the location of the closure device as a discontinuous target volume.

15. The arrangement according to claim 1, wherein additional cooling means are provided for the closure device or dividing wall.

16. The arrangement according to claim 1, wherein the target flow, as a target flow that can be made available in a reproducible manner, reaches the location of the closure device as a discontinuous target volume.

17. The arrangement according to claim 1, wherein the target flow is present in the interaction region in a liquid or solidified aggregate state.

18. The arrangement according to claim 17, wherein a liquefied gas or gas mixture is provided for forming the target flow in the target nozzle.

19. The arrangement according to claim 18, wherein the target flow contains at least one inert gas, preferably xenon.

20. The arrangement according to claim 17, wherein the target flow contains liquid metal or a liquid metal compound.

21. The arrangement according to claim 20, wherein the target flow contains tin.

22. The arrangement according to claim 17, wherein the target flow is a saline solution.

23. The arrangement according to claim 17, wherein the target flow comprises fluoro-fomblin.

24. The arrangement according to claim 1, wherein the energy beam for plasma generation is a laser beam.

25. The arrangement according to claim 1, wherein the energy beam for plasma generation is an electron beam.

26. The arrangement according to claim 1, wherein the energy beam for plasma generation is an ion beam.

* * * * *